US008563303B2

(12) United States Patent
Fieder et al.

(10) Patent No.: US 8,563,303 B2
(45) Date of Patent: Oct. 22, 2013

(54) METHOD FOR INCREASING RECLONING EFFICIENCY

(75) Inventors: Jüergen Fieder, Biberach (DE); Lore Florin, Biberach (DE); Hitto Kaufmann, Ulm (DE); Thomas Krieg, Warthausen (DE); Melanie Briegel, Altheim (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 23 days.

(21) Appl. No.: 12/922,945

(22) PCT Filed: Mar. 16, 2009

(86) PCT No.: PCT/EP2009/053091
§ 371 (c)(1),
(2), (4) Date: Mar. 29, 2011

(87) PCT Pub. No.: WO2009/115495
PCT Pub. Date: Sep. 24, 2009

(65) Prior Publication Data
US 2011/0230642 A1    Sep. 22, 2011

(30) Foreign Application Priority Data

Mar. 19, 2008 (EP) ..................... 08152974

(51) Int. Cl.
C12N 5/02 (2006.01)
C12N 5/07 (2010.01)
C12N 5/18 (2006.01)

(52) U.S. Cl.
USPC ........... 435/325; 435/358; 435/360; 435/326; 435/70.3

(58) Field of Classification Search
None
See application file for complete search history.

(56) References Cited

U.S. PATENT DOCUMENTS 5,262,308 A * 11/1993 Baserga ................. 435/69.1
6,340,574 B1 * 1/2002 Hunt et al. ................. 435/69.1
6,413,744 B1 * 7/2002 Morris et al. ............... 435/69.1
7,833,787 B2 * 11/2010 Otto et al. .................... 435/358
8,021,881 B2 * 9/2011 Reiter et al. ................. 435/404

FOREIGN PATENT DOCUMENTS

WO    2006/047380 A    4/2006

OTHER PUBLICATIONS

Rasmussen et al., Cytotechnology 1998, 28, 31-42.*
Hamilton et al., In Vitro. Sep. 1977;13(9):537-547.*
Pak et al., Cytotechnology vol. 22, Issue 1-3, 1996. pp. 139-146.*
Riss et al., In Vitro Cell Dev Biol. vol. 24, Issue 11, Nov. 1988 pp. 1099-1106.*
Gasser et al., In Vitro Cell Dev Biol. Oct. 1985;21(10):588-592.*
Sunstrom et al., Biotechnol Prog. Sep.-Oct. 2000;16(5):698-702.*
International Search Report corresponding to priority application PCT/EP2009/053091 dated Apr. 8, 2009.
Sawada, K, et al. "Human Colony-Forming Units-Erythroid Do Not Require Accessory Cells, But Do Require Direct Interaction with Insulin-Like Growth Factor I and/or Insulin for Erythroid Development"; Journal of Clinical Investigation, American Society for Clinical Investigation, US; vol. 83 (May 1, 1989) pp. 1701-1709.
Sunstrom, N, et al., "Recombinant Insulin-Like Growth Factor-I (IGF—I) Production in Super-CHO results in the expression of IGF-I receptor and IGF Binding Protein 3"; Cytotechnology, Kluwer Acadamic Publishers, DO, vol. 28, No. 1-3, (Sep. 1, 1989), pp. 91-99.

* cited by examiner

Primary Examiner — Daniel C Gamett
(74) Attorney, Agent, or Firm — Michael P. Morris; Usha R. Patel

(57) ABSTRACT

The present invention relates to the field of cell culture technology and relates to methods of replicating/cloning cells, preferably cell lines which are important for the production of biopharmaceuticals. The invention also relates to methods of preparing proteins using cells that have been obtained and replicated by single cell deposition and compositions which make it possible to replicate individual cells.

By using IGF particularly in conjunction with HSA in the culture medium after recloning, the recloning efficiency and hence the quantity of clones obtained can be increased significantly.

17 Claims, 4 Drawing Sheets

METHOD FOR INCREASING RECLONING EFFICIENCY

BACKGROUND TO THE INVENTION

1. Technical Field

The present invention relates to the field of cell culture technology and relates to methods of replicating/cloning cells, preferably cell lines which are important for the production of biopharmaceuticals. The invention also relates to methods of preparing proteins using cells that have been obtained and replicated by single cell deposition and compositions which make it possible to replicate individual cells.

2. Background

The market for biopharmaceuticals for treating humans is growing fast throughout the world at a rate of 270 new biopharmaceuticals which are currently being tested in clinical trials with an estimated potential turnover of 30 billion in 2003 (Werner 2004).

At present, an ever increasing number of biopharmaceuticals are produced in mammalian cells, as these have the capability for the correct processing and modification of a human protein. The successful production of high yields of biopharmaceuticals in mammalian cells is therefore crucial and depends on the characteristics of the recombinant monoclonal producing cell line that is used in the manufacturing process. In addition the duration of the cell line development is a critical time factor as to how quickly the biopharmaceutical can enter into clinical trials. In view of these aspects there is an urgent need to speed up the process of developing cell lines and make it more efficient.

For the biotechnological production of biologically active or therapeutic proteins in mammalian cells, so-called biopharmaceuticals, the corresponding mammalian cells are stably transfected with DNA which codes for the biologically active protein (or its subunits). After the transfection process a pool of millions of differently transfected cells is normally obtained. Therefore the crucial step for the preparation of efficient production cell lines is in the selection and replication of cell clones which on the one hand grow very stably and on the other hand show a high specific productivity of therapeutic protein (product formation etc.). As there are millions of different product-expressing cells, it is critical to be able to analyse a plurality of cells individually with a high throughput and using automation in order to be able to sort out suitable candidates (single cell clones) which both grow very robustly and also yield high product titres. This process of single cell isolation and subcultivation is known as cloning or recloning.

The use of animal cell cultures for producing biopharmaceuticals demands a genotypically and phenotypically homogeneous, i.e. monoclonal cell culture. This is achieved by recloning techniques such as "limited dilution" or by the automated depositing of individual cells by fluorescence activated cell sorting (FACS).

However, there is the problem of effectively replicating typical recombinant production cells such as mouse myeloma (NS0), hamster ovary (CHO), or hamster kidney cells (BHK), particularly if they are adapted to growth in serum-free suspension cultures, i.e. under modern production-relevant cell culture conditions, after recloning, whereby the cells are individually deposited in microtitre plates, under serum-free culture conditions.

The reason for this is that cells in vivo are embedded in the tissue matrix and are supplied with secreted auto- and paracrine growth factors by adjacent cells. They are therefore not adapted to isolated growth and die off without stimulation by growth factors if they are not slowly adapted to the new conditions.

In particular, the use of serum-free or chemically defined media in the recloning step leads to a restricted recloning efficiency, i.e. only a small percentage of the cells deposited survive and grow into a monoclonal cell line.

The "limited dilution" and FACS recloning techniques currently used are well known in the art.

In "limited dilution" the cell suspension is serially diluted and the cells are then deposited in a microtitre plate in different numbers of cells per well. In wells containing large numbers of cells, many or all the cells survive as the result of adequate secretion of autocrine growth factors. The fewer cells are seeded per well, the fewer cells survive, so that in this way the dilution can be adjusted so that statistically only one cell survives per well and grows into a monoclonal line.

These individual cells clones are detected by visual and/or imaging techniques and the cell clones are grown on in larger culture vessels.

In FACS technology, a flow cytometer is used to generate single cell clones. For this the cells are placed in a laminar flow and are individually steered into the wells of the microtitre dishes. This ensures that the surviving colonies really are individual clones. Therefore, FACS technology is the preferred method compared with Limited Dilution.

The use of serum-free or chemically defined media in the recloning step leads to restricted recloning efficiency, i.e. only a few percent of the individually deposited cells grow into a monoclonal cell line.

At a low recloning efficiency, therefore, a number of microtitre plates have to be filled with single cells in order to obtain the desired number of individual clones, which is time-consuming and expensive (e.g. in terms of media, dishes, etc).

A low recloning efficiency is particularly disadvantageous if the subsequent analysis of the single cell clones is to be carried out using an automated system. An analysing robot cannot normally distinguish between wells containing living or dead cells and automatically measures all the wells in the microtitre plate. With a recloning efficiency of only 10%, this means that in 90% of cases the robot will analyse an empty well—and will use the same amount of reagent for this as for analysing a living cell clone. In the example here, therefore, 90% of the time and 90% of the material costs are wasted without any data being obtained.

To solve this problem, in the past, serum (e.g. foetal calf serum, FCS) has often been added to the medium. Serum contains an undefined mixture of different soluble proteins and growth factors which support the survival and proliferation of cells. For regulatory reasons, however, the use of non-definable additions such as serum is increasingly less tolerated, partly because of the risk of infection with bovine viruses. Totally serum-free production of cell lines is therefore the state of the art from a regulatory point of view.

Another possible solution is to carry out a "limited dilution" for the recloning. As this method only leads statistically to the production of single cell clones but many clones may also grow in one well, this process has to be repeated several times (usually 2-3 times) to ensure that the cell line obtained really does originate from only a single clone. These repeated cycles involve high labour and time costs which have a negative effect on the costs and timelines required.

Another approach is the use of "feeder" cells. The name comes from the English word "feed" and refers to a co-cultivation with usually non-dividing cells which serve to supply the desired cells in the culture with nutrients and secreted growth factors.

The recloning efficiency can be significantly increased by feeder cells. However, a disadvantage of this method is the high cost of generating the feeder cells parallel to the actual single cell deposition. Moreover, there is no guarantee of reproducibility as the quality of the feeder cells, their secretion activities and vitality after the arresting of growth are very difficult to standardise. In addition, the presence of feeder cells may have an adverse effect in automated clone analysis or may even make it impossible, by falsifying the results, depending on the nature of the assay used.

The aim of the present invention is to increase the recloning efficiency in the serum-free FACS-based cloning of production cells.

The invention is also based on increasing the recloning efficiency without the use of feeder cells.

SUMMARY OF THE INVENTION

The technical problem of reduced recloning efficiency in serum-free, preferably chemically defined medium is solved by the addition of IGF (insulin-like growth factor) or insulin to the medium.

The recloning efficiency and hence the quantity of clones obtained can be significantly increased by the use of IGF or insulin in the culture medium after recloning. This effect has been observed at concentrations starting from 100-500 μg/L IGF or 50-100 mg/L insulin in the cloning medium. The effect of IGF on the recloning efficiency is significantly higher than that of insulin. The use of IGF in insulin-free medium is therefore a preferred embodiment.

With regard to the recloning efficiency, optimum curves are observed both with insulin and with IGF. The optimum for insulin is 100 mg/L and for IGF it is 500 μg/L. The level of recloning efficiency is higher when using IGF.

The positive effect of IGF optionally with feeder cells and albumin, particularly HSA, on recloning efficiency is observed in various cell lines and cell types such as for example hamster and murine cells, as well as human and various other cell systems.

Moreover, the addition of albumin, particularly serum albumin (HSA), to the culture medium brings about an increase in recloning efficiency. A significant effect is visible even with low concentrations of albumin, particularly HSA, upwards of 100 mg/L and can be further increased by higher albumin/HSA concentrations of 400-1000 mg/L. In particular, a positive effect is observed with the addition of 500 mg/L of albumin/HSA.

Figure 2:
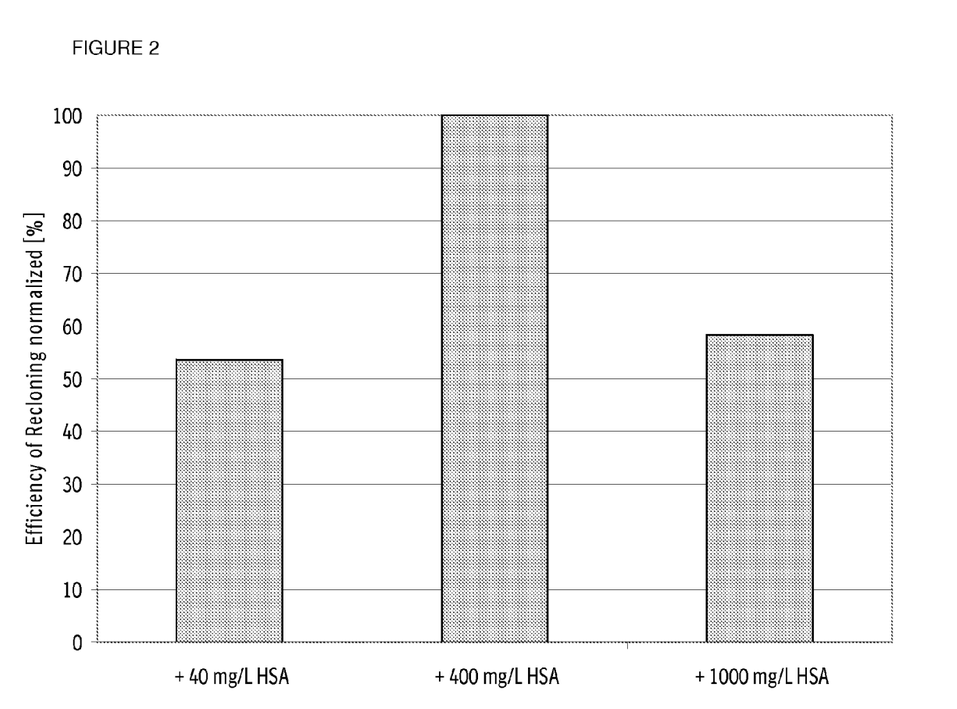
Figure 3:
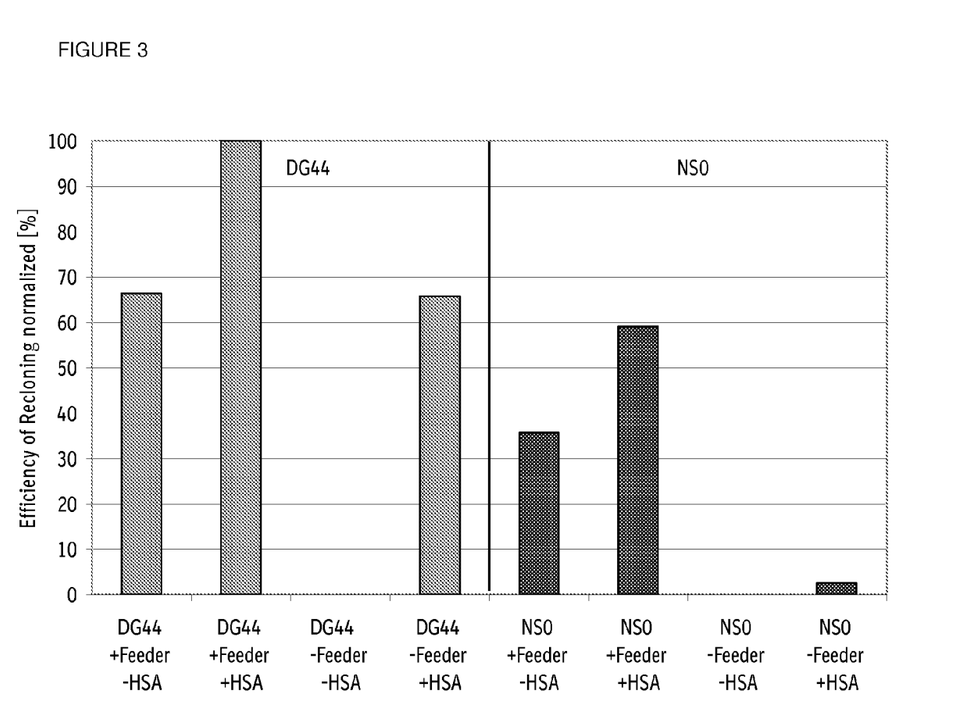

The optimum concentration of albumin/HSA in IGF-containing medium (without an insulin supplement) is below 1000 mg/l (cf. FIGS. 2, 3 and 4). The optimum concentration of albumin/HSA is in the range from 300-600 mg/l or 400-600 mg/l, preferably in the range from 400-500 mg/l, particularly preferably 400 mg/l. Also particularly preferred is an albumin/HSA concentration of 500 mg/l.

The albumin/HSA source used may be purified human material, recombinant material (from pro- or eukaryotes) or recombinant plant material.

An albumin/HSA-dependent increase in recloning efficiency is observed both in the presence and absence of feeder cells in various cell lines.

The highest recloning efficiency may be obtained by means of a combination of these approaches, i.e. the addition of IGF and albumin/HSA to a serum- and insulin-free culture medium. Feeder cells may optionally additionally be used depending on the nature of the subsequent analysis method.

The method described here for increasing the recloning efficiency in serum-free media by the addition of IGF or insulin and optionally albumin/HSA results in a more effective clone screening and thereby in a more efficient cell line development process.

In biopharmaceutical development, the primary goal of recloning is to identify high-producing cell clones. A higher recloning efficiency, through the broader base of clones obtained, and as a result of a normal distribution of the clones in terms of productivity, leads to a higher probability of obtaining high-producing cell clones.

As fewer cells have to be deposited in dishes at a higher recloning efficiency in order to obtain the same number of living cell clones, there is also a significant saving in both time and effort as well as costs as a result. The process step is thus more economical overall.

Moreover, the increased recloning efficiency forms the basis for the use of highly efficient automated clone screening methods (screening robot).

In systems of this kind there is generally no selection of individual wells in the microtitre plate, but all are measured equally, irrespective of whether they contain a living cell population or not. As a result of all the wells in the plate being analysed the number of clones examined increases in direct proportion to the number of emergent clones. A recloning efficiency of only 10% means that 90% of the wells are empty and therefore cannot supply any usable data but are still analysed. In terms of economy, this means that in 90% of cases time and money in the form of reagents are expended without any data being gained. Therefore the efficiency of high throughput automation systems for early clone selection increases proportionally with the number of clones obtained after the depositing of single cells.

Another advantage of the method described is that the addition of IGF or insulin and optionally albumin/HSA increases the recloning efficiency to a point where there is no need for feeder cells.

On the one hand this reduces the effort involved in producing and pre-cultivating the feeder cells and at the same time increases the reproducibility of the single cell cloning. In addition it makes it possible to use technologies for visually detecting the number of living cells as a tool for clone analysis. As the amount of product in the culture medium is in linear correlation with the number of producing cells, the technological development seeks to detect both the amount of product and the number of cells, so as to determine from these the highest producing cell clones.

As feeder cells are difficult to distinguish visually from the emergent production cells, they are also included in the visual determination of cell numbers, leading to an inaccurate calculation of the total number of cells and hence of the specific productivity. A process without feeder cells is therefore advantageous and represents a preferred embodiment.

Possible applications for the method described can be found particularly in the production of biopharmaceuticals.

The increase in the recloning efficiency in the generation of production cells for biopharmaceutical production leads to a higher probability of a highly-productive clone and hence an improved or accelerated product development.

The process also increases the economy of this step and also makes it possible to use high-throughput automated clone analysing techniques.

The prior art describes the use of special media compositions for increasing recloning efficiency (WO2006047380). Insulin is described as an essential ingredient. However, in the present patent application the use of IGF instead of insulin is mentioned as an alternative and superior possibility. Furthermore, the data of the present application show that by combining IGF (preferably <800 µg/l or 100-500 µg/l) and albumin, particularly HSA (preferably <1000 mg/l or 300-600 mg/l, most preferably 400-500 mg/l) in an insulin-free medium, the recloning efficiency can be improved still further. The concentrations of albumin (particularly HSA) in the present patent application are less than 1000 mg/l and hence significantly lower than those in the above-mentioned patent specification WO2006047380.

DESCRIPTION OF THE FIGURES

FIG. 1:

Influence of IGF compared with insulin on the recloning efficiency in HSA supplemented medium.

DG44 cells are cultured for at least five passages in five varying media which contain 5 different concentrations of IGF or insulin. Then individual cells are cloned using FACS. After 21 days the growing clones are counted and the recloning efficiency is determined. For simplicity, the recloning efficiency is standardised, i.e. the highest value obtained is set at 100%.

FIG. 2:

Influence of HSA supplementation on the recloning efficiency in serum-free and insulin-free medium.

DG44 cells are cultured for at least five passages in BI's own medium (containing 50 µg/l IGF but no insulin), which is supplemented with different concentrations of HSA (40, 400 and 1000 mg/l) and with feeder cells. Then individual cells are cloned using FACS. After 21 days the growing clones are counted and the recloning efficiency is determined. For simplicity, the recloning efficiency is standardised, i.e. the highest value obtained is set at 100%.

FIG. 3

Recloning efficiency in cell lines DG44 in BI's own medium (containing 50 µg/l IGF, no insulin supplement) and NS0 in commercial CD hybridoma medium from Invitrogen (containing IGF in a concentration of less than 800 µg/l, no insulin supplement) with and without feeder cells and with and without 500 mg/l HSA supplementation in the medium. DG44 and NS0 cells are cultured in the corresponding media over at least five passages. Then individual cells are cloned using FACS. After 21 days the growing clones are counted and the recloning efficiency is determined. For simplicity, the recloning efficiency is standardised, i.e. the highest value obtained is set at 100%.

FIG. 4

Recloning efficiency in cell line DG44 (cultured in BI's own medium without an insulin supplement) with 50 µg/l or 500 µg/l IGF supplement and with or without 500 mg/l HSA supplement in the medium.

DG44 cells are cultured in the corresponding media over at least five passages. Then individual cells are cloned using FACS. After 21 days the growing clones are counted and the recloning efficiency is determined. For simplicity, the recloning efficiency is standardised, i.e. the highest value obtained is set at 100%.

DETAILED DESCRIPTION OF THE INVENTION

Definitions

Before the more detailed description of the invention by means of the non-restrictive exemplifying embodiments that follow, it should be pointed out that the use of the indefinite article, for example "a" or "an" and the definite article, namely "the", includes both the singular and plural of the term in question, unless one of the two forms is explicitly ruled out and reference is made to a particular form (singular or plural). Thus, the term "a cell" automatically includes "a plurality of cells" as well, unless it is explicitly stated that only a single cell is meant. The singular is explicitly meant, for example, where "a" or "one" is supplemented by (1).

The term "insulin" is known to the skilled man. There are a number of different insulin molecules (Gilman, A. G. et al., Eds., The Pharmacological Basis of Therapeutics, Pergamon Press, New York, 1990, pp. 1463-1495). One form of insulin is zinc insulin, for example. Human zinc insulin or recombinant insulin is frequently used in cell culture. The concentration of insulin can be measured in the culture medium using routine experiments such as a commercially obtainable insulin-specific ELISA.

The term "insulin-free" means that the culture medium does not contain any insulin, particularly any recombinant insulin and no insulin is added to it either.

Albumin is the most commonly occurring protein in the plasma. It is produced in the liver and contributes to maintaining osmotic pressure in the blood. Albumin binds to nutrients and metabolites and thereby helps to transport them.

In serum-containing cell culture media albumin is often the dominant component of the serum. A preferred embodiment of the present invention provides a biochemically defined, serum-free and insulin-free medium for cloning single cells, which contains serum albumin.

The term "albumin" in the present invention denotes a polypeptide component which has the biological activity of albumin. Albumin generally denotes animal albumin, particularly a mammalian albumin such as for example human, bovine, equine, murine, rat-type and porcine albumin and albumin from birds such as chickens, in particular, etc. Preferably the albumin is human serum albumin (HSA). Preferably, the albumin is not obtained from a natural animal source (serum). Particularly preferred is recombinant or synthetic albumin, particularly recombinant HSA.

The production of recombinant HSA is well known in the prior art and can be carried out e.g. using genetically modified yeasts (U.S. Pat. No. 5,612,197). Recombinant HSA may be obtained commercially from various suppliers, for example from Sigma-Aldrich (Recombinant HSA, Cat. No. A-7223).

The concentration of HSA can be determined by routine methods such as a commercially obtainable ELISA (e.g. "Human Albumin ELISA Quantitation Kit", Bethyl Laboratories, Montgomery, Tex.)

According to this embodiment of the present invention the cell culture medium contains recombinant albumin in a sufficient concentration to allow the growth of a single cell, particularly a single CHO cell. For example, recombinant albumin is present in the medium in a concentration of about 100 mg/L to about 1000 mg/L, preferably in a concentration of approximately 300 mg/L to approximately 800 mg/L and most preferably in a concentration of approximately 500 mg/L.

The term "cloning/recloning", "clone/reclone" in connection with cell culture means a technique by means of which a cell population of identical cells can be obtained from an original cell. The term "cell cloning" or "single cell cloning" thus means a process wherein single cells can be identified and isolated from a cell pool with cells of different genotypes and then replicated to form a cell population consisting of a plurality of genetically identical cells. If the cells are deposited individually, i.e. only one (1) cell per culture vessel, and then expanded to form a cell population of identical cells, the process is "direct single cell cloning". If a number of cells are simultaneously deposited in a culture vessel, expanded to form a cell population and this is divided up into cell populations of identical cells by repeated dilution (=limited dilution), this is described as an "indirect cloning" method.

"Single clones" or "single cell clones" or "clones" for short are genetically identical cells which originate from one (1) single cell. A cell population consisting of identical cells of the same origin is consequently referred to hereinafter as a "monoclonal cell population". If during the cultivation of cells of the same origin there are spontaneous changes in the genome, for example mutations and/or translocations, the individual cells of this cell population are still regarded as identical cells for the purposes of the present invention, and the culture is regarded as a monoclonal cell population. By contrast, a pool of stably transfected cells (transfectants) are not cell clones of the same lineage, i.e. they are not a monoclonal cell population, even if genetically identical starting cells are transfected with an identical nucleic acid.

The term "subclones/subcultures" refers to different generations of cells which are produced from an original cell or original culture by single or multiple passaging of the dividing cells. The words "subclones/subcultures" are used, for example, when identical cells or cell cultures are cultivated and replicated over a number of generations.

The term "cloning efficiency" or "recloning efficiency" is defined as the percentage of cells which survive, divide and form vital cell populations after being deposited. If for example in a cell sorting operation 100 cells are distributed over 100 culture vessels and if 25 of these 100 individually deposited cells grow to form cultures, the cloning efficiency is 25%.

By "effective or efficient recloning" is meant a cloning efficiency of at least 10%, preferably at least 20%, more preferably at least 30% and even more preferably at least 40%. According to a particularly preferred embodiment of the present invention the term effective recloning means cloning with an efficiency of at least 50%, preferably at least 60%, most preferably at least 70% and even more preferably at least 80%.

The term "capable of division/expandable" for the purposes of the present invention describes the potential of a cell/cell population to divide endlessly but at the least over 2, preferably 4, passages. This potential may for example be reduced or destroyed altogether by irradiation with $^{[137]}$Cs or by mitomycin C treatment.

The term "derivative/descendant" refers to cells which can be traced back genetically to a particular starting cell and are formed for example by subcultivation (with or without selection pressure) and/or generated by gene manipulation. Re-isolations of cells of the same cell type are also included in the term "derivative/descendant". Thus, for example, all CHO cell lines are derivatives/descendants of the hamster ovary cells isolated from *Cricetulus griseus* by Puck et al., 1958, regardless of whether they were obtained by subcultivation, re-isolation or gene manipulations.

The term "feeder cell" comes from the English word "feed" and refers to a co-cultivation with usually non-dividing cells which serve to supply the desired cells in the culture with nutrients and secreted growth factors. For the preparation, living cells are growth-arrested by irradiation with UV or gamma radiation or treatment with Mitomycin C. The resulting feeder cells live and produce and secrete growth factors but are unable to divide further.

The term "autologous feeder cell" means that both the feeder cell and the cell which is to be cultivated in the presence of this feeder cell are derived taxonomically from the same origin. If for example the cell to be cultivated is a hamster cell (subfamily Cricetinae), preferably a cell of the genus *Cricetulus* or *Mesocricetus*, for example a CHO or BHK cell, each feeder cell originally isolated from this subfamily is a feeder cell which is autologous to these hamster cells of the subfamily Cricetinae.

According to a preferred embodiment the term "autologous feeder cell" means that both the feeder cell and the cell which is to be cultivated were derived from the same genus taxonomically or were originally isolated from the same genus (cells from *Cricetulus* or *Mesocricetus*). If for example the cell to be cultivated is a hamster cell of the genus *Cricetulus* or *Mesocricetus*, preferably a CHO or BHK cell, each feeder cell originally isolated from the genus in question is an autologous feeder cell in the sense of this invention.

According to another preferred embodiment an autologous feeder cell is present if the feeder cell and the cell to be cultivated come from the same species, for example *Cricetulus griseus* or *Mesocricetus auratus*. According to a particularly preferred embodiment an autologous feeder cell is present if both the feeder cell and the cell to be cultivated come from the same species and have the same tissue tropism (e.g. ovarian cells from *Cricetulus griseus*—CHO cells).

According to a particularly preferred embodiment a feeder cell is an autologous feeder cell if both the feeder cell and the cell to be cultivated originate from the same basic cell, for example if both cells were originally CHO-DG-44 cells or descendants of these cells. According to another preferred embodiment the feeder cell confers the same resistances, e.g. to antibiotics, as the cell which is to be cultivated. This is particularly advantageous when the cell deposition is carried out in the presence of a selecting agent, e.g. an antibiotic.

The term "limited dilution" denotes an alternative method of recloning. A cell suspension is serially diluted and the cells are then deposited in a microtitre plate in different numbers of cells per well. In wells with high numbers of cells, many or all of the cells will survive as the result of adequate secretion of autocrine growth factors. The fewer cells are seeded per well, the fewer cells survive, which means that the dilution can thus be adjusted so that statistically only one single cell per well survives and grows into a monoclonal line. As this method only leads statistically to the formation of single cell clones, but it is possible for several clones to grow in one well, this process has to be repeated several times (normally 2 to 3 times) in order to ensure that the cell line obtained really is from a single clone.

In FACS technology a Fluorescence-Activated Cell Sorter (Flow Cytometer) is used to generate single cell clones. For this, the cells are brought into a laminar flow and each individually steered into the wells in the microtitre plates. This ensures that the surviving colonies really are single clones. Therefore FACS technology is the preferred method, compared with limited dilution.

The term "serum" denotes the cell-free component of the blood. Serum contains an undefined mixture of different soluble proteins and growth factors that assist the survival and proliferation of cells. For the cell culture, foetal calf serum (FCS) or bovine serum (FBS) are predominantly used. The usual concentration ranges are 10-20% FCS or FBS as an addition to the cultivation medium.

The term "serum-free" means culture media and also cultivation conditions which are characterised in that cells are grown in the absence of animal and/or human serum, preferably in the absence of any proteins isolated from serum, preferably in the absence of non-recombinantly produced proteins. Consequently, the term "cells adapted to serum-free conditions" means those cells which can be replicated in the absence of animal or human serum or serum proteins.

The term "protein-free" means that the culture medium does not contain any animal proteins; proteins isolated from bacteria, yeasts or fungi are not regarded as animal proteins.

The term "chemically defined" describes a cell culture medium which is serum-free, preferably also protein-free, and which consists of chemically defined substances. Chemically defined media thus consist of a mixture of predominantly pure individual substances. One example of a chemically defined medium is the CD-CHO medium produced by Messrs Invitrogen (Carlsbad, Calif., US).

The expression "a cell which may be cultivated in suspension" refers to cells which are adapted to growth in liquid cultures ("suspension cultures") and whose ability to adhere to the surfaces of vessels, for example cell culture dishes or flasks, has been restricted or lost. Cells which are adapted both to serum-free growth and to growth in suspension are referred to as "non-adherent cells adapted to serum-free medium". If feeder cells are prepared from such cultures, these cells are by definition "non-adherent feeder cells adapted to serum-free medium".

By "conditioned medium" is meant medium from a culture of living cells which is filtered and added to the fresh medium in the seeding-out microtitre plates. The activity of the conditioned medium is based on its content of growth factors which have been secreted into the medium by the cells of the preliminary culture and have thereby "conditioned" it. Conditioned medium clearly has a positive influence on the recloning efficiency. The increases achieved are minor, however, and as the sole measure are not sufficient for practical use. A preferred embodiment of the invention consists in the use of conditioned medium for increasing the recloning efficiency particularly after FACS-based depositing of single cells.

Protein/Product of Interest:

Biopharmaceutically significant proteins/polypeptides comprise e.g. antibodies, enzymes, cytokines, lymphokines, adhesion molecules, receptors and the derivatives or fragments thereof, but is not restricted thereto. Generally, all polypeptides that act as agonists or antagonists and/or have a therapeutic or diagnostic use are significant. Other proteins of interest are for example proteins/polypeptides that are used to alter the properties of host cells within the scope of so-called "Cell Engineering", such as e.g. anti-apoptotic proteins, chaperones, metabolic enzymes, glycosylation enzymes, and the derivatives or fragments thereof, but are not restricted thereto.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity. In addition, the polypeptides may multimerise and form homo- and heteromers.

By recombinant proteins are meant proteins that are produced by recombinant expression in host cells. Such recombinant proteins are produced under the strictest conditions of purity in order to minimise the risk of contamination. Recombinant proteins are usually produced in suitable host cells such as e.g. yeast cells, animal cells or prokaryotic cells (*E. coli* or other bacterial strains) using an expression vector such as for example a purified plasmid, a bacteriophage, an isolated DNA, mRNA, viruses or another nucleic acid, to introduce the recombinant protein into the host cell and allow it to integrate into the host cell chromosome therein. Eukaryotic expression systems are preferred as they typically have the necessary cell machinery for correctly modifying, processing and folding complex mammalian proteins such as antibodies. Recombinant HSA is obtainable for example from various commercial suppliers such as Sigma Aldrich.

Examples of therapeutic proteins are insulin, insulin-like growth factor, human growth hormone (hGH) and other growth factors, receptors, tissue plasminogen activator (tPA), erythropoietin (EPO), cytokines, e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN)-alpha, -beta, -gamma, -omega or -tau, tumour necrosis factor (TNF) such as TNF-alpha, -beta or -gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments. The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')2 fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cystein groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia-, tri- and pentabodies).

The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphite bridges. Examples of diabodies can be found in the literature.

The term minibody is used in the art to denote a bivalent homodimeric scFv derivative. It consists of a fusion protein which contains the CH3 region of an immunoglobulin, preferably IgG, most preferably IgG1, as dimerisation region.

This connects the scFv fragments by means of a hinge region, also of IgG, and a linker region.

The term triabody is used in the art to denote a trivalent homotrimeric scFv derivative. The direct fusion of VH-VL without the use of a linker sequence leads to the formation of trimers.

The fragments known in the art as mini antibodies which have a bi-, tri- or tetravalent structure are also derivatives of scFv fragments. The multimerisation is achieved by means of di-, tri- or tetrameric coiled coil structures.

The term "antibody fusion" or "antibody fusion protein" denotes the fusion/coupling of a protein to an antibody or part of an antibody. In particular these include fusion proteins produced by genetic engineering, in which a therapeutic protein is coupled to the Fc part of an antibody, in order to increase the half-life/stability of the protein in the serum. The term also encompasses antibody fusions consisting of a peptide and an antibody or part of an antibody.

Host Cells:

Preferred host cells for the purposes of the invention are hamster cells such as BHK21, BHK TK⁻, CHO, CHO-K1, CHO-DUKX, CHO-DUKX B1 and CHO-DG44 cells or derivatives/descendants of these cell lines. Particularly preferred are CHO-DG44, CHO-DUKX, CHO-K1 and BHK21 cells, particularly CHO-DG44 and CHO-DUKX cells. Also suitable are myeloma cells from the mouse, preferably NS0 and Sp2/0 cells and derivatives/descendants of these cell lines.

Examples of hamster and mouse cells which can be used according to the invention are given in Table 1 that follows. However, derivatives and descendants of these cells, other mammalian cells including but not restricted to cell lines of humans, mice, rats, monkeys, rodents, or eukaryotic cells, including but not restricted to yeast, insect, bird and plant cells, may also be used as host cells for the production of biopharmaceutical proteins.

TABLE 1

Hamster and mouse production cell lines

| Cell line | Accession number |
| --- | --- |
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO-K1 | ATCC CCL-61 |
| CHO-DUKX (=CHO duk⁻, CHO/dhfr⁻) | ATCC CRL-9096 |
| CHO-DUKX B1 | ATCC CRL-9010 |
| CHO-DG44 | Urlaub et al., Cell 33[2], 405-412, 1983 |
| CHO Pro-5 | ATCC CRL-1781 |
| Lec13 | (Stanley P. et al, 1984). |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| Per.C6 | (Fallaux, F. J. et al, 1998) |
| CHL | ECACC No. 87111906 |

According to the invention, recombinant mammalian cells, preferably rodent cells, most preferably hamster cells such as CHO or BHK are particularly preferred.

Preferred host cells are those which are established, adapted and cultivated totally under serum-free conditions. Particularly preferably the host cells are additionally established, adapted and cultivated totally in a medium that is not only serum-free but also free from any animal proteins/peptides.

Examples of suitable nutrient solutions include commercially obtainable media such as Ham's F12 (Sigma, Deisenhofen, DE), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S (Invitrogen), serum-free CHO-Medium (Sigma) and protein-free CHO-Medium (Sigma).

The term "production cell" or "producer cell" or "production clone" denotes a cell that is used in a process for preparing a protein. In particular this includes genetically modified cells that are used for the industrial production of recombinant proteins. Within the scope of this invention, the term includes in particular genetically modified eukaryotic host cells which express a recombinant protein and are used to prepare this protein. This includes in particular monoclonal cell lines for the production of therapeutic proteins.

Embodiments

The present invention describes a method or process of cultivating a (1) single cell comprising the following steps:
(a) cultivating a cell population,
(b) isolating a (1) single cell from the said cell pool and
(c) cultivating the said single cell in a serum-free and insulin-free medium which contains "insulin-like growth factor" (IGF).

In a special embodiment the method according to the invention is characterised in that the medium contains IGF in a concentration of less than 800 µg/l. Other preferred concentration ranges for IGF are 50-750 µg/L, and particularly preferably 250-750 µg/L. Ideally, the IGF concentration is 500 µg/L.

In a preferred embodiment the method according to the invention is characterised in that the isolation of the single cells is carried out by FACS.

In another embodiment the method according to the invention is characterised in that the cell originates from an established immortalised cell line. In another embodiment the cell is a recombinant cell, i.e. it is a genetically modified cell. In a preferred embodiment the cell is a cell that produces recombinant or heterologous proteins. This preferred embodiment thus relates to a production cell which is used in biopharmaceutical protein production.

Thus the present invention relates in particular to a method/process for culturing a (1) single recombinant production cell, comprising the following steps:
a) cultivating a cell population,
b) isolating a (1) single recombinant production cell from said cell pool by FACS and
c) cultivating the said single cell in a serum-free and insulin-free medium which contains "insulin-like growth factor" (IGF) in a concentration range of 250-750 µg/l (preferably 500 µg/l).

In another embodiment the method according to the invention is characterised in that the cell is a non-human cell, preferably a hamster or mouse cell. In a specific embodiment the method according to the invention is characterised in that the cell is a rodent cell, preferably a hamster or mouse cell.

In a preferred embodiment the method according to the invention is characterised in that the cell is a "Chinese Hamster Ovary" (CHO) cell. Another preferred cell is the NS0 cell. In another embodiment the method according to the invention is characterised in that the said cell is a eukaryotic cell such as, for example, a yeast, plant, worm, insect, bird, fish, reptile or mammalian cell. Particularly preferably the cell is an avian cell from chickens or ducks. Particularly preferred is a eukaryotic cell which is a vertebrate cell, particularly a mammalian cell.

In another embodiment the method according to the invention is characterised in that the said mammalian cell is a Chinese Hamster Ovary (CHO), a monkey-type kidney cell CV1, a monkey-type kidney cell COS, a human lens epithelial cell PER.C6™, a human embryonic kidney cell HEK293 or a human myeloma cell, a human amniocyte cell, a baby hamster kidney cell, an African green monkey kidney cell, a human cervical carcinoma cell, a dog kidney cell, a rat liver cell, a human lung cell, a human liver cell, a murine breast cancer cell or if it is a myeloma cell, a canine, porcine or macaque cell or a cell obtained from rats, rabbits, hares, cats or goats.

In another preferred embodiment the method according to the invention is characterised in that the said cell is a CHO wild-type cell, a CHO K1 cell, a CHO DG44 cell, a CHO DUKX-B11 cell, a CHO Pro-5 cell or a mutant or a derivative thereof. Also particularly preferred are the CHO mutants Lec1 to Lec35. The CHO DG44 cell is most particularly preferred.

In another embodiment the method according to the invention is characterised in that the medium additionally contains albumin. Recombinant albumin or human serum albumin (HSA) is preferred. Human recombinant serum albumin is particularly preferred.

In a special embodiment the method according to the invention is characterised in that albumin is present in a concentration of less than 1 g/L. The optimum concentration of albumin/HSA in IGF-containing medium (without an insulin supplement) is below 1000 mg/l (cf. FIGS. 2, 3 and 4). Other preferred concentration ranges for albumin/HSA are 250-999 mg/L, 250-900 mg/l and 250-750 mg/L. A concentration of 400 mg/l and 500 mg/L albumin, particularly recombinant human serum albumin, is particularly preferred. The optimum concentration of albumin/HSA is in the range from 300-600 mg/l or 400-600 mg/l, preferably in the range from 400-500 mg/l.

In another embodiment the method according to the invention is characterised in that the single cell is cultured in the presence of feeder cells. They are preferably autologous feeder cells, particularly preferably autologous CHO feeder cells.

In another embodiment the method according to the invention is characterised in that the isolation of a (1) single cell in step b) is carried out by "limited dilution" or using a "fluorescence activated cell sorting" (FACS) apparatus. It is particularly preferable to isolate a (1) single cell using FACS.

In another embodiment the method according to the invention is characterised in that the cell(s) in step a), b) and c) express(es) a protein of interest.

In a preferred embodiment the method according to the invention is characterised in that the protein of interest is a therapeutic protein, preferably an antibody, an antibody fusion protein or an antibody fragment.

In a special embodiment the method according to the invention is characterised in that the protein of interest is a membrane-located or a secreted protein, preferably an antibody, an antibody fusion protein or an antibody fragment.

The said antibody is preferably a monoclonal, polyclonal, mammalian, murine, chimeric, humanised, primatised, primate or human antibody or an antibody fragment or derivative thereof such as for example an immunoglobulin light chain, an immunoglobulin heavy chain, an immunoglobulin light and heavy chain, a Fab fragment, a F(ab')2 fragment, an Fc part, an Fc-Fc fusion protein, an Fv fragment, a single chain Fv fragment, a single domain Fv fragment, a tetravalent single chain Fv fragment, a disulphide-linked Fv fragment, a domain-deleted antibody or fragment, a minibody, diabody, or a fusion polypeptide of one of the above-mentioned fragments with another peptide or polypeptide, an Fc-peptide fusion, an Fc-toxin fusion or a scaffold protein.

A preferred embodiment of the invention comprises the use of conditioned medium in order to increase the recloning efficiency particularly after FACS-based deposition of a single cell.

In a preferred embodiment the method according to the invention is characterised in that conditioned medium is used. Conditioned medium is used in particular as a base medium or as a medium additive in steps a) and/or b) and/or c). Preferably, conditioned medium is used in step c). In particular, conditioned medium is used in step c) as the base medium or as a medium additive. The proportion of conditioned medium may be from 10-100% of the total volume of medium; a proportion of 30-75%, particularly preferably 50%, consists of conditioned medium.

The present invention also relates to a cell which is generated by a method according to the invention.

The present invention preferably also relates to a method for producing a protein of interest in a cell, preferably a CHO cell, under serum-free and insulin-free culture conditions, comprising the following steps:
  a) preparing a cell population containing a gene of interest that codes for a protein of interest,
  b) culturing these cells under culture conditions that permit cell growth,
  c) isolating a single cell and depositing it in a container, preferably in a 96-well dish,
  d) culturing the said single cell in serum-free and insulin-free medium containing IGF, optionally in the presence of albumin and/or feeder cells,
  e) selecting a cell according to its level of expression of a protein of interest,
  f) harvesting the protein of interest for example by separating the cell constituents from the supernatant and
  g) purifying the protein of interest.

In a special embodiment the process according to the invention is characterised in that in step d) autologous feeder cells are preferably used.

Also preferred is a process in which the culture conditions include an IGF concentration of less than 800 µg/l. The IGF concentration is preferably in the range between 50-750 µg/L, and particularly preferably in the range between 250-750 µg/L. Ideally the IGF concentration is 500 µg/L.

Also preferred is a process in which the culture conditions comprise an albumin (especially HSA) concentration of less than 1000 mg/l. The albumin concentration is preferably in the range between 250-999 mg/L, 250-900 mg/l and 250-750 mg/L. Particularly preferred is a concentration of 400 mg/l and 500 mg/L albumin, particularly recombinant human serum albumin. The optimum concentration of albumin, particularly HSA, is in the range from 300-600 mg/l or 400-600 mg/l, preferably in the range from 400-500 mg/l.

In another special embodiment, the process according to the invention is characterised in that the isolation of a single cell in step c) is carried out by FACS.

Also preferred is an embodiment of the process in which CHO DG44 cells are used.

In a particularly preferred embodiment, the process according to the invention is characterised in that step e) is automated. In particular in e) an analysing robot is used.

An automated process of this kind is particularly characterised in that the automated system consists of:
i) a (robot) station which carries out FACS-based single cell cloning,
ii) an incubator for culturing the cells after the single cell cloning has taken place, connected to
iii) a robot station which carries out an assay for detecting protein, particularly antibodies, such as for example an ELISA or HTRF® (homogenous time resolved fluorescence) assay.

Particularly preferred is an automated process that enables steps c) to e) to be carried out in 96- or 384-well plates.

It is also preferable to carry out automatic screening for recombinant protein production in the cloned cells as early as possible, e.g. before the first passaging of the cells (immediate early screen) as described in PCT/EP2007/059663 (=EP1901068). This application is hereby incorporated by reference. It is also preferable to carry out an automatic process which has a throughput of at least 250 measurements within 12 hours, particularly preferably at least 500, 2000, 4000, 10000 or 14000 measurements within 12 hours.

In a particular embodiment the method according to the invention is characterised in that the protein of interest is a recombinant protein.

In a preferred embodiment the method according to the invention is characterised in that the protein of interest is a therapeutic protein, preferably an antibody, an antibody fusion protein or an antibody fragment.

In a particular embodiment the method according to the invention is characterised in that the protein of interest is a membrane-located protein or a secreted protein, preferably an antibody, an antibody fusion protein or an antibody fragment.

The said antibody is preferably a monoclonal, polyclonal, mammalian, murine, chimeric, humanised, primatised, primate or human antibody or an antibody fragment or a derivative thereof such as for example an immunoglobulin light chain, an immunoglobulin heavy chain, an immunoglobulin light and heavy chain, a Fab fragment, a F(ab')2 fragment, an Fc part, an Fc-Fc fusion protein, an Fv fragment, a single chain Fv fragment, a single domain Fv fragment, a tetravalent single chain Fv fragment, a disulphide-linked Fv fragment, a domain-deleted antibody or fragment, a minibody, diabody, or a fusion polypeptide of one of the above-mentioned fragments with another peptide or polypeptide, an Fc-peptide fusion, an Fc-toxin fusion or a scaffold protein.

The present invention thus relates in particular to a method for producing a protein of interest, preferably an antibody, in a recombinant production cell, preferably a CHO cell, under serum-free and insulin-free culture conditions, comprising the following steps:
a) preparing a cell population containing a gene of interest that codes for a protein of interest,
b) culturing these cells under serum-free culture conditions that permit cell growth,
c) isolating a single cell and depositing it in a container, preferably in a 96-well dish, using FACS,
d) culturing the said single cell in serum-free and insulin-free medium containing IGF in a concentration of less than 800 µg/l or in a range from 250-750 µg/l, preferably 500 µg/l, preferably in the presence of albumin in a concentration of less than 1000 mg/l and/or feeder cells,
e) selecting a cell according to its level of expression of a protein of interest, this selection preferably being carried out using a robot station that performs a protein- or antibody-detecting assay, such as e.g. ELISA or HTRF® (homogenous time resolved fluorescence), in which the throughput is at least 250 measurements within 12 hours, particularly preferably at least 500, 2000, 4000, 10000 or 14000 measurements within 12 hours,
f) harvesting the protein of interest for example by separating the cell constituents from the supernatant and
g) purifying the protein of interest.

The present invention further relates to a protein which is prepared by a method according to the invention.

The present invention further relates to a process for selecting a production cell using a method according to the invention as described above in various embodiments.

In one specific embodiment the production cell according to the invention is characterised in that it is selected by one of the methods described according to the invention.

In a preferred embodiment the production cell according to the invention is characterised in that the host cell is a hamster or murine cell.

In a preferred embodiment the production cell according to the invention is characterised in that the host cell is a hamster cell or a mouse myeloma cell, preferably a CHO or BHK cell or an NSO cell. A CHO DG44 cell is particularly preferred.

The present invention further relates to the use of a production cell according to the invention for biopharmaceutical protein manufacture.

The present invention also relates to a serum-free and insulin-free culture medium which allows a (1) single cell to be cultured, containing IGF (preferably <800 µg/l, or 250-750 µg/l, particularly 500 µg/l) and optionally albumin (preferably <1000 mg/l or 300-600 mg/l or 400-500 mg/l). Preferably, the single cell is a CHO cell, most preferably a CHO DG44 cell.

The following Examples are of a non-restrictive nature. They merely constitute possible embodiments. The skilled man can readily adapt or transfer the conditions described therein to other embodiments.

EXPERIMENTAL SECTION

Equipment and Methods

Cultivation of the Cells

The cells CHO-DG44/dhfr$^{-/-}$ (Urlaub et al., 1983) are permanently cultivated as suspension cells in serum-free Ex-Cell medium (JRH, USA) supplemented with hypoxanthine and thymidine or BI's own medium in cell culture flasks at 37° C. in a damp atmosphere and 5% $CO_2$. The cell counts and viability are determined with a CEDEX Cell Counter (Innovatis, DE) or by tryptan blue staining and the cells are then seeded in a concentration of $1-3\times10^5$/mL and run every 2-3 days. Recombinant CHO-DG44 are used for the single cell cloning. The cultivation of cloned recombinant cells is carried out analogously to these cells. Again, Ex-Cell medium (JRH, USA) or BI's own medium without hypoxanthine and thymidine is used as the medium.

The cells NS0 can be permanently cultivated as suspension cells in serum-free hybridoma medium, animal component-free medium (Sigma, Aldrich, St. Louis, USA) in cell culture flasks at 37° C. in a damp atmosphere and 5% $CO_2$. The cell counts and viability can be determined with a CEDEX Cell Counter (Innovatis, DE) or by tryptan blue staining and the cells are then seeded in a concentration of $1-3\times10^5$/mL and run every 2-3 days.

Preparation of Feeder Cells by Irradiation

Suspended CHO-cells (untransfected cells) growing without serum and protein are centrifuged at 180 g for 10 minutes and adjusted to a cell concentration of $1\times10^6$/mL in HBSS (Hank's balanced salt solution).

Then the cells are irradiated with a radioactive irradiation source (Cs137-irradiator, Gammacell 2000, made by Molsgaard Medical NS, Denmark) with an energy dose delivery of 4 Gy/min. After the irradiation the cells are seeded with about 10000 cells per well in 96-well microtitre plates in the Ex-Cell medium (JRH, USA) specific for the cells or BI's own medium (e.g. TH-9) and stored at about 37° C. and 5% $CO_2$ in an incubating chamber atmosphere.

The process is carried out accordingly with NS0 cells, while the feeder cells are kept/seeded in the particular medium specific for the cells.

Preparation of Conditioned Medium

The conditioned medium is obtained from the supernatant of a CHO cell culture. The CHO cells are put in at a seeding density of $0.3 \times 10^6$ cells/mL and cultured for 2-4 days. The supernatant is separated from the cells by centrifugation and then sterile-filtered through a 0.2 μm filter. The filtrate obtained is used as the conditioned medium.

FACS-Based Cell Deposition

The automatic cell deposition (single or multiple cell deposition) is carried out with a Flow Cytometer (Coulter EPICS Altra (Messrs. Beckman-Coulter, Miami, Fla., USA) fitted with an argon laser (488 nm) using an Autoclone unit. The cells are centrifuged off in the exponential growth phase and taken up in HBSS to obtain a cell concentration of $1-1.5 \times 10^7$/mL. Then the cells are sorted using the "Hypersort Option" at a speed of 8000-12000 cells/second according to their position in the scattered light. Cells that express a fluorescent protein may alternatively be sorted according to their fluorescence intensity in relation to the intracellularly expressed fluorescence protein. The cells are each individually deposited in 96-well microtitre plates (optionally) provided with feeder cells. During the sorting of CHO cells the cells are deposited in Ex-Cell medium (JRH, USA) or BI's own medium (e.g. TH-9) with the corresponding supplements of IGF or insulin and optionally or preferably HSA.

For NS0 cells the cell deposition is carried out accordingly in hybridoma medium, animal component-free medium (Sigma, Aldrich, St. Louis, USA).

Calculating the Recloning Efficiency

The recloning efficiency is calculated from the quotient of positive wells per plate to total number of wells per plate. The definition of positive wells is those in which there is exactly one clone.

Example 1

Figure 1:
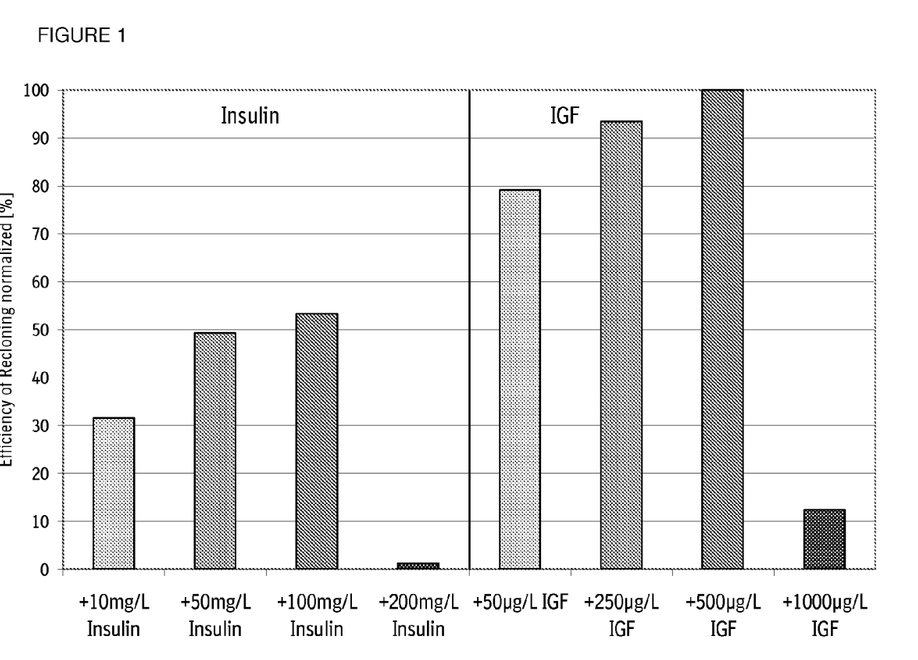

Effect of Insulin and IGF on the Recloning Efficiency in HSA-Supplemented Medium CHO DG44 cells are adapted for 5 passages to BI's own serum-free medium. Then a FACS-based single cell deposition is carried out with different concentrations of insulin and IGF in medium supplement with 500 mg/L HSA. After 21 days the emergent clones are counted and from this the recloning efficiency is calculated by means of the proportion of clones that have grown out of the total number of wells used. Optimum curves are observed both with insulin and with IGF. The optimum for insulin is 100 mg/L and for IGF it is 500 μg/L. (FIG. 1) The level of recloning efficiency when using IGF is higher than with insulin.

Example 2

Influence of the Addition of HSA in the Medium on the Recloning Efficiency

CHO DG44 cells are adapted for 5 passages to the basal medium ExCell 302 or BI's own medium (containing 50 μg/l IGF, but no insulin supplement). Then a FACS-based single cell deposition is carried out with different concentrations of HSA with and without feeder cells. After 21 days the emergent clones are counted and from this the recloning efficiency is calculated by means of the proportion of clones that have grown out of the total number of wells used. The use of HSA is found to have a positive effect, while an added amount of HSA of about 400 mg/L is sufficient or optimum (FIG. 2). FIG. 2 shows that the optimum HSA concentration in IGF-containing medium (without an insulin supplement) is less than 1000 mg/l.

Example 3

Influence of the Use of HSA-Supplemented Medium on the Recloning Efficiency of CHO DG44 and NS0 Cells CHO DG44 and NS0 cells are adapted for 5 passages to BI's own medium (CHO DG44) or CD-hybridoma medium (Invitrogen). Then a FACS-based single cell deposition is carried out with and without feeder cells and with and without 500 mg/L HSA. After 21 days the emergent clones are counted and from this the recloning efficiency is calculated by means of the proportion of clones that have grown out of the total number of wells used. (FIG. 3).

In both cell lines feeder cells and HSA are found to have a positive effect on the recloning efficiency of the two cell types. The recloning efficiency is higher in the CHO DG44 cells than in the NS0 cells.

Example 4

Influence of the Combination of HSA and IGF on the Recloning Efficiency

With the cells of a CHO-DG44 culture a FACS-based single cell deposition is carried out with feeder cells with different concentrations of HSA and IGF. After 21 days the emergent clones are counted and from this the recloning efficiency is determined.

Figure 4:
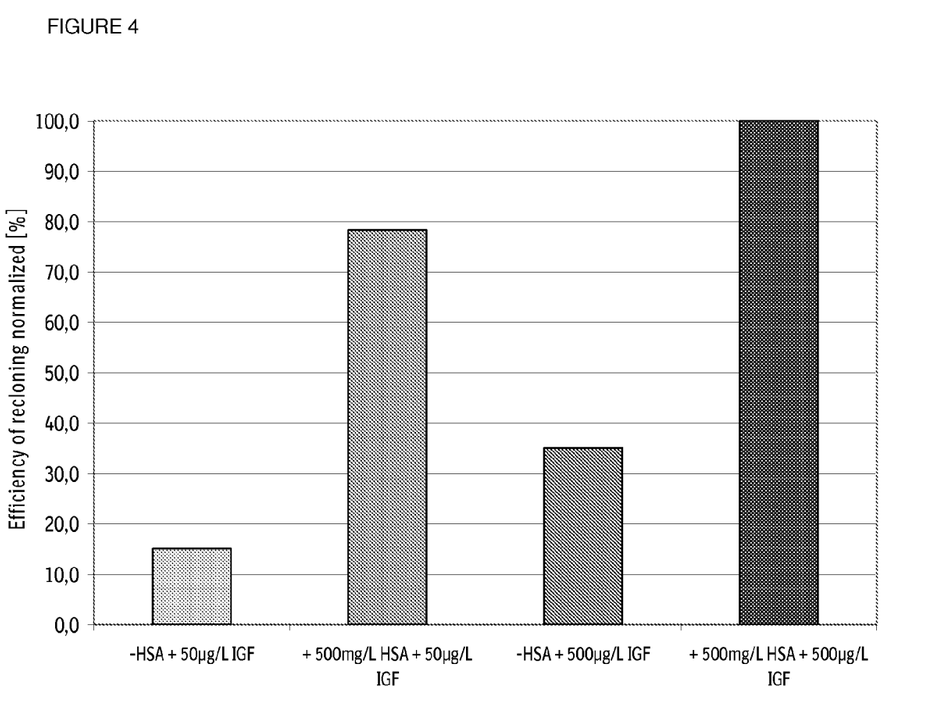

FIG. 4 shows a concentration-dependent increase in recloning efficiency, both for HSA and for IGF. In addition, HSA and IGF are found to have an additive or synergistic effect. Accordingly, the highest recloning efficiency is achieved when both proteins (500 mg/L HSA and 500 μg/L IGF) are added to the culture medium.

The invention claimed is:

1. A method of culturing a single cell, comprising the following steps:
   a) culturing a cell population,
   b) isolating a single cell from said cell population and
   c) culturing the said single cell in a serum-free and insulin-free medium which contains "insulin-like growth factor" (IGF),
   wherein the said cell is a hamster or murine cell.

2. The method according to claim 1, characterised in that IGF is present in a concentration of less than 800 μg/l.

3. The method according to claim 1 characterised in that the cell is a "Chinese Hamster Ovary" (CHO) cell.

4. The method according to claim 1 characterised in that the medium additionally contains albumin.

5. The method according to claim 4 characterised in that albumin is present in a concentration of less than 1 g/L.

6. The method according to claim 1 characterised in that the single cell is cultured in the presence of feeder cells.

7. The method according to claim 6 characterised in that they are autologous feeder cells.

8. The method according to claim 1 characterised in that the isolation of a single cell in step b) is achieved by "limited dilution" or using a "fluorescence activated cell sorting" (FACS) apparatus.

9. The method according to claim 1 characterised in that the cell(s) in step a), b) and c) express(es) a protein of interest.

10. The method according to claim 9 characterised in that protein of interest is a therapeutic protein selected from an antibody, an antibody fusion protein and an antibody fragment.

11. The method according to claim 1 characterised in that conditioned medium is added.

12. A process for selecting a production cell, using a method according to claim 1.

13. A method of manufacturing a biopharmaceutical protein comprising purifying a protein expressed by the production cell made by the method of claim 1.

14. A process for producing a protein of interest in a cell, preferably a CHO cell, under serum-free and insulin-free culture conditions, comprising the following steps:

a) preparing a cell population containing a gene of interest that codes for a protein of interest,
b) culturing these cells under culture conditions that permit cell growth,
c) isolating a single cell and depositing it in a container, selected from a 96-well dish or a 384 well dish,
d) culturing the said single cell in serum-free and insulin-free medium containing IGF, optionally in the presence of albumin and/or feeder cells,
e) selecting a cell according to its level of expression of a protein of interest,
f) harvesting the protein of interest by separating the cell constituents from the supernatant and
g) purifying the protein of interest.

15. The process according to claim 14 characterised in that the protein of interest is a recombinant protein.

16. The process according to claim 14 characterised in that the protein of interest is a therapeutic protein.

17. The process according to claim 16 characterised in that the protein of interest is an antibody or an antibody fusion protein or an antibody fragment.

* * * * *

UNITED STATES PATENT AND TRADEMARK OFFICE
CERTIFICATE OF CORRECTION

| | | |
|---|---|---|
| PATENT NO. | : 8,563,303 B2 | Page 1 of 1 |
| APPLICATION NO. | : 12/922945 | |
| DATED | : October 22, 2013 | |
| INVENTOR(S) | : Fieder et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this
Twenty-first Day of April, 2015

Michelle K. Lee
*Director of the United States Patent and Trademark Office*